(12) United States Patent
Camus

(10) Patent No.: US 7,302,040 B2
(45) Date of Patent: Nov. 27, 2007

(54) DEVICE FOR MEDICAL PROVISION

(75) Inventor: Estelle Camus, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/455,262

(22) Filed: Jun. 16, 2006

(65) Prior Publication Data

US 2006/0285644 A1  Dec. 21, 2006

(30) Foreign Application Priority Data

Jun. 17, 2005 (DE) .................. 10 2005 028 215

(51) Int. Cl.
*H05G 1/08* (2006.01)
(52) U.S. Cl. ................... 378/117; 378/198
(58) Field of Classification Search ............ 378/117, 378/195–198, 205, 102, 210; 600/407, 410, 600/415, 424
See application file for complete search history.

(56) References Cited

U.S. PATENT DOCUMENTS 5,821,920 A  10/1998  Rosenberg et al.
5,878,112 A * 3/1999 Koertge ................ 378/209
6,219,604 B1  4/2001  Dilger et al.
6,723,106 B1  4/2004  Charles et al.
2001/0016517 A1 * 8/2001 Nishiumi et al. .......... 463/36

FOREIGN PATENT DOCUMENTS

| DE | 36 04 955 C2 | 8/1987 |
| DE | 695 32 536 T2 | 10/1997 |
| DE | 199 12 169 A1 | 7/2000 |
| DE | 699 18 569 T2 | 9/2001 |

* cited by examiner

*Primary Examiner*—Hoon Song

(57) ABSTRACT

An x-ray arm of an x-ray system is controlled with the aid of a joystick. If there is a threat of a collision between the x-ray arm and an obstacle, for example a patient bed, a force is exerted on the guide element which generates a warning signal perceptible in a tactile manner, which indicates to the user the danger of a collision.

11 Claims, 3 Drawing Sheets

DEVICE FOR MEDICAL PROVISION

CROSS REFERENCE TO RELATED APPLICATIONS

This application claims the benefits of German Patent application No. 10 2005 028 215.6 filed Jun. 17, 2005 and is incorporated by reference herein in its entirety.

FIELD OF THE INVENTION

The invention relates to a device for medical provision of a patient with:
- a medical functional unit which can be controlled by a user and is moveable in relation to a patient bed,
- a position sensor, which detects the position of the functional unit, and with
- a monitoring device connected downstream from the position sensor which monitors the movement of the functional unit and, if there is a danger of a collision with an obstacle, generates a warning signal perceptible to the user.

BACKGROUND OF THE INVENTION

Such a device is known from DE 36 04 955 C2. The known device is an x-ray diagnostic device which features a moveable C-arm on the ends of which an x-ray detector and an x-ray emitter respectively are mounted. The C-arm can be moved in relation to the support table for the patient to be examined. The movement of the C-arm is monitored with potentiometers and limit switches. The analog measurement signals delivered by the potentiometers are converted with the aid of analog-digital converters into digital values and passed to a microcomputer, which determines the current position of the C-arm from these values and checks whether the C-arm or the components mounted on it are touching a fictitious envelope surface stretched over the support table. In this case an acoustic or optical warning signal is generated. This indicates to the user, who is controlling the movement of the C-arm at an operating console, that there is the threat of a collision. Furthermore the movement of the C-arm can be halted or the speed of the movement reduced if the C-arm is approaching the fictitious envelope surface.

One disadvantage of the known device is that optical signals can easily be overlooked since the user also has to take account of other optical information communicated during the movement of the C-arm. Although acoustic signals are not as a rule missed, an acoustic signal which lasts for a longer period can drown out other important acoustic signals, for example the acoustic signals of an electrocardiograph. In addition the patient becomes restless, generally assuming that a malfunction has occurred.

SUMMARY OF THE INVENTION

Using this prior art as its starting point, the object of the invention is thus to create a device for medical provision of a patient in which the danger of a collision is communicated in a clearly perceptible manner.

This object is achieved by a device with the features of the independent claim. Advantageous embodiments and developments are specified in its dependent claims.

The outstanding feature of the device is that the guidance device features a guidance element which can be actuated by the user exerting a force on it and that the monitoring device, if there is a danger of a collision, operates mechanically via a setting device on the guidance element to generate a signal which can be perceived as tactile feedback by the user.

If the user of the device wishes to move the medical functional unit the user must come into contact with the guidance element in order to be able to exert a force on the guidance element. If however there is a danger of a collision, the setting device acts mechanically on the guidance element. This action is perceived by the user who is in contact with the guidance element. With the device the user is thus always warned if he wishes to have a movement of the medical functional unit performed. The warning is thus always issued at the relevant time in addition the warning is only issued to the user wishing to undertake the movement of the medical functional unit. No other personnel who are present or the patient are disturbed by the warning. Furthermore the meaning of the warning signal is intuitively clear to the user, by contrast with conventional devices in which the user must first establish a relationship between the acoustic or optical warning signal and the danger of collision.

In a preferred embodiment the adjusting device makes the guidance element vibrate. Preferably the amplitude of the vibration increases as the danger of a collision increases. The vibrations communicate the danger of a collision directly to the user.

In a further preferred embodiment the setting device is an inhibiting device which acts against the force exerted by the user on the guidance element. Preferably the inhibiting force increases as the danger of the collision increases.

This embodiment offers the advantage of effectively preventing incorrect control of the movement of the medical functional unit. This is because a movement of the guidance element which would lead to a collision between the medical functional unit and an obstacle can be suppressed by the inhibiting device. In addition the danger of a collision can be intuitively communicated to the user.

To allow the warning signal to be output at an early stage before or during the movement of the medical functional unit, in addition to a position signal from the position sensor, a control signal from the guidance device is applied to the monitoring unit. This makes it possible before or during the movement of the medical functional unit to restrict the movement and thereby to prevent a collision of the medical functional unit with an obstacle.

The device can be especially advantageously used in conjunction with an x-ray system in which an x-ray source and an X-ray detector are mounted at the ends of a C-shaped arm respectively.

Furthermore the guidance element is preferably a joystick which can be operated manually. Complex movements can be controlled with this type of joystick. In addition a control device can operate a joystick mechanically in a simple manner.

BRIEF DESCRIPTION OF THE DRAWINGS

Further properties and advantages of the invention can be taken from the description below in which exemplary embodiments of the invention are explained in detail with reference to the enclosed drawing. The figures show.

DETAILED DESCRIPTION OF THE INVENTION

Figure 1:
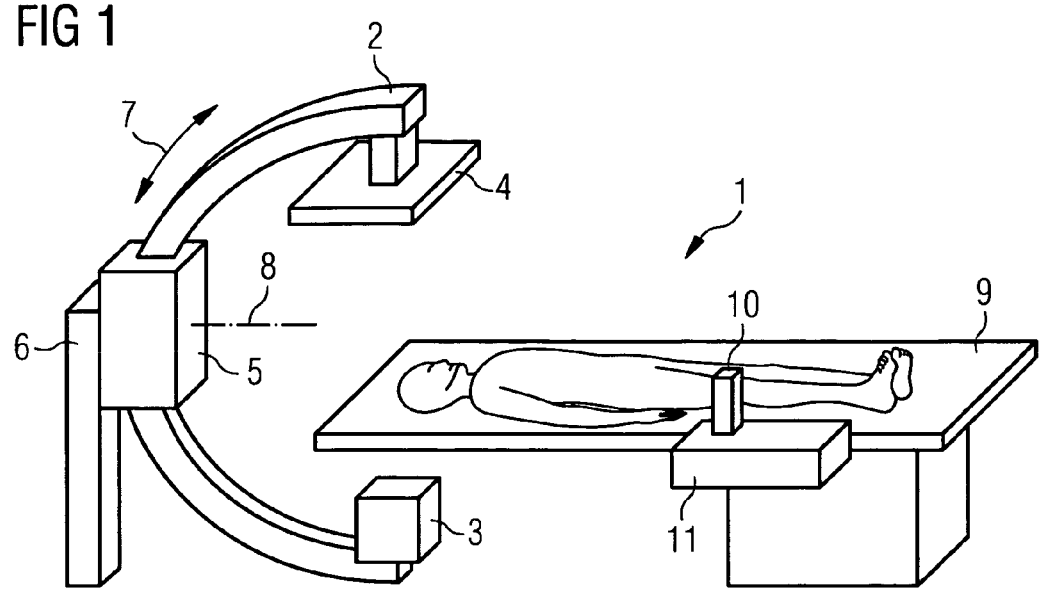
FIG. 1 a perspective view an x-ray system which is used in angiography or cardiography.

The x-ray system 1 comprises a C-shaped x-ray arm 2, on the ends of which an x-ray source 3 and an x-ray detector 4 are mounted. The x-ray arm 2 is held by a support 5 which is mounted on a stand 6 The x-ray arm 2 can be moved in the support 5 in a circular direction 7. Furthermore the support 5 is mounted on the stand 6 so that it can pivot around an axis 8. Finally the stand 6 can also be moved around the floor.

During operation of the x-ray system 1 the x-ray arm 2 is both moved in the circular direction 7 and also rotated around the pivot axis 8. In this case the x-ray arm 2 executes a relative movement in relation to a patient bed 9. The x-ray arm 2 is controlled amongst other methods with the aid of a joystick 10 of a guidance device 11. For example the x-ray arm 2 will always move in the circular direction 7 if the joystick 10 is pushed to the left or to the right. In this case the x-ray arm 2 performs a rotational movement if the joystick 10 is pushed forwards or backwards.

Figure 2:
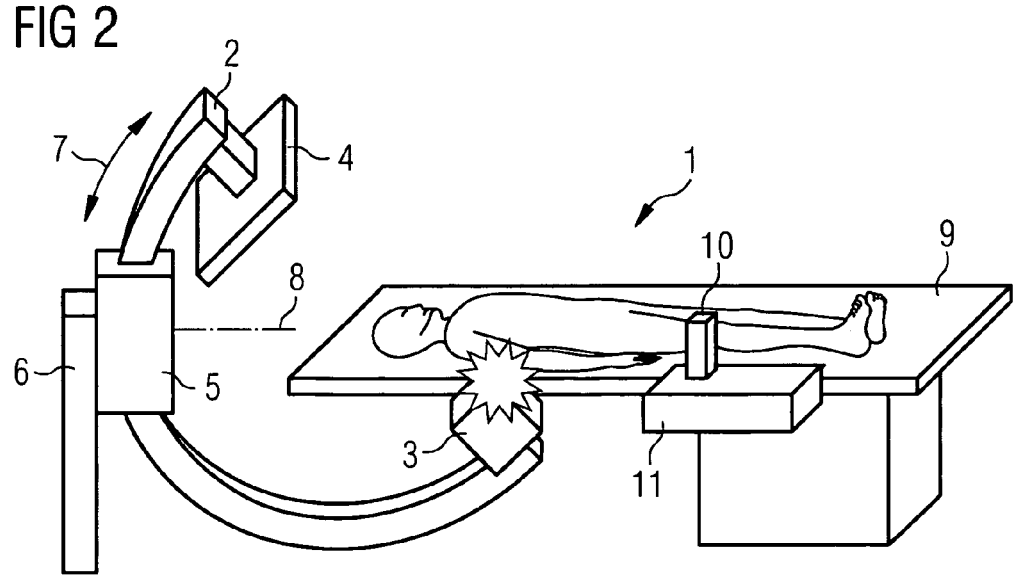
FIG. 2 the x-ray system from FIG. 1 in a state in which there is a danger of a collision with the patient bed.

If the x-ray system 1 is used for the treatment of a patient 12 lying on the patient bed 9, the personnel are frequently busy operating on the patient 12. Thus their full attention is as a rule not available for the control of the x-ray arm 2. Thus, as shown in FIG. 2, there is always the danger of the collision 13 between the x-ray arm 2 and the components mounted thereon and the patient bed 9. In addition there can also be collisions between the x-ray arm 2 and the components mounted thereon and further obstacles, such as further functional units arranged in the area of the patient bed 9. These types of functional units can for example be magnets for magnetic navigation of a catheter equipped with a magnetic tip in the body of the patient 12.

Devices have thus been developed which record a possible collision and avoid this where possible. These devices are known to the person skilled in the art as such and are not the subject of this application.

by contrast with the prior art, the x-ray system 1 warns the user who is manually operating the joystick 10, not by using an additional acoustic or optical signal, but by tactile means.

Figure 3:
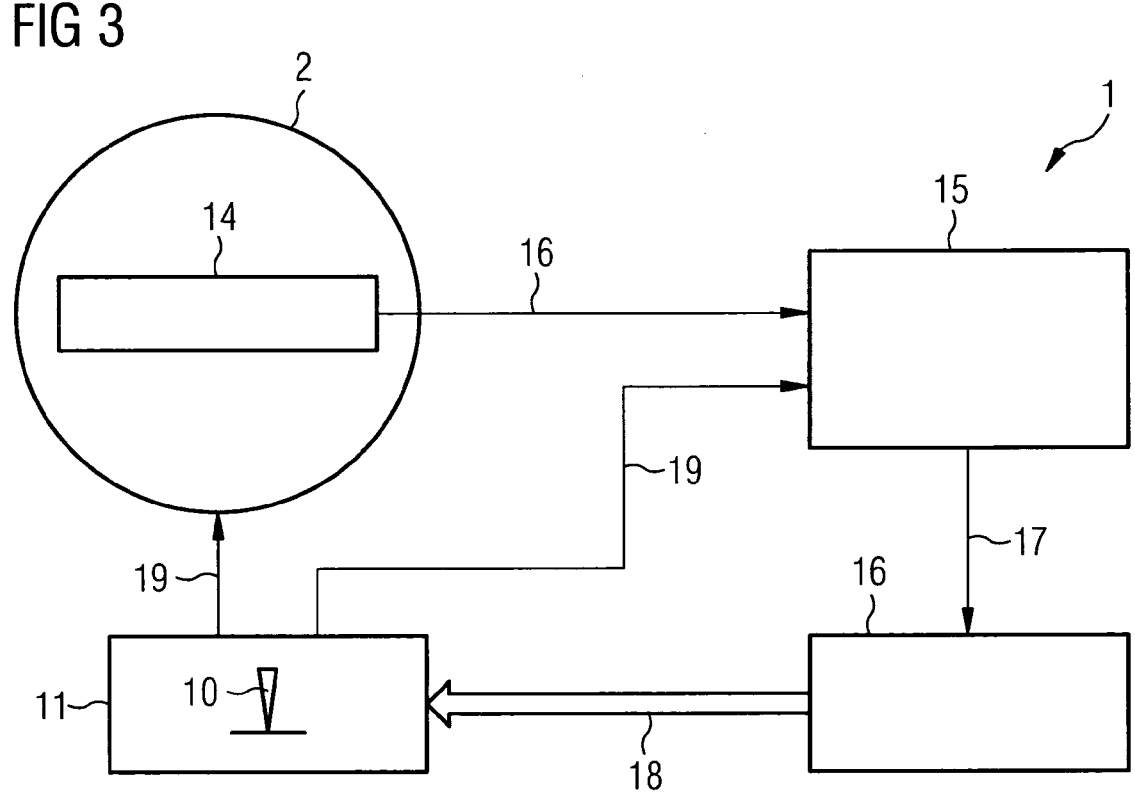
FIG. 3 a block diagram of a circuit for controlling the x-ray system from FIGS. 1 and 2.

FIG. 3 shows a block diagram of the x-ray system 1. A position sensor 14 monitors the movement of the x-ray arm 2. The position sensor 14 applies a position signal 16 to the monitoring device 15. If the monitoring device 15 establishes the threat of a collision 13, a setting device 16 is used to output an activation signal 17. The setting device 16 exerts a force effect 18 on the joystick 10 of the guidance device 11. The force effect 18 can result in or can cause an oscillation or vibration of the joystick 10 so that the force exerted by the user on the joystick 10 is inhibited. The latter has the advantage that the user, as a result of the inhibition of the movement of the joystick 10, cannot move the joystick 10 in a direction which would lead to a collision 13 between the x-ray arm 2 and an obstacle.

It should be pointed out that the guidance device 11 not only applies a control signal 19 to the setting devices for the x-ray arm, but will preferably also forward the control signal 19 to the monitoring device 15 so that the monitoring device can check whether the desired movement of the x-ray arm through activation of the joystick 10 leads to a collision.

It should further be pointed out that the intensity of the force effect 18 advantageously depends on the level of the danger of a collision. The force effect 18 increases as the danger of a collision 13 increases.

Figure 4:
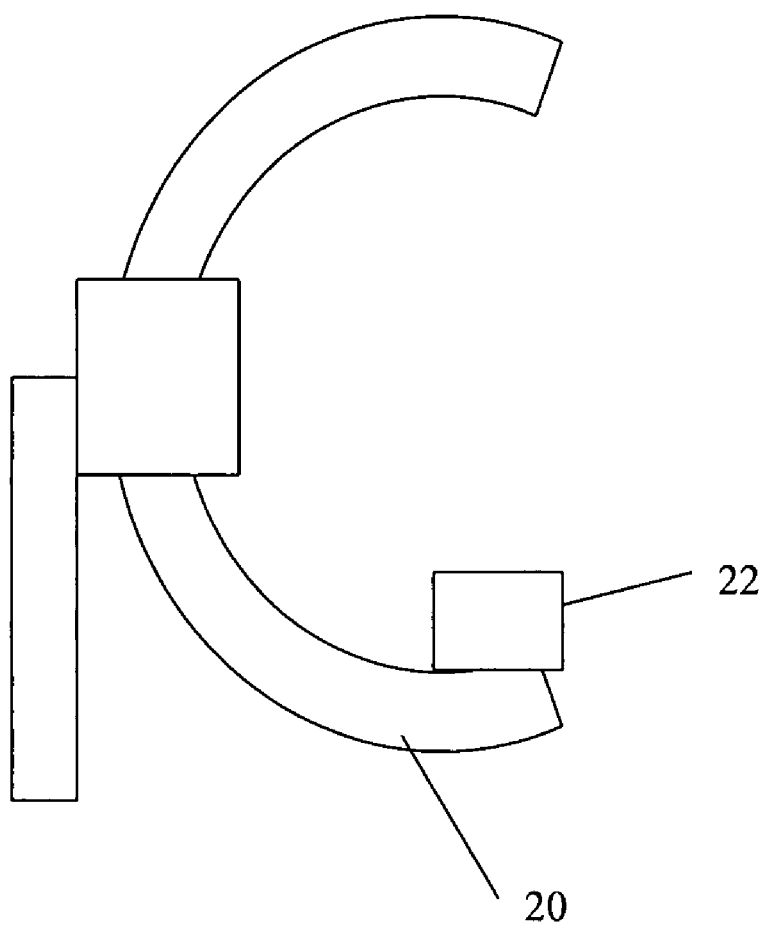
FIG. 4 shows a side view of an embodiment implementing a magnetic navigation system.

FIG. 4 shows an alternative embodiment, similar to embodiment in FIG. 1. The support arm 20 has mounted thereon a magnet 22 in place of an x-ray source.

Finally it should also be pointed out that, instead of the joystick 10, modified control elements can also be used. For example a joystick 10 can be replaced by a tracker ball let into a recess, of which the movement is detected by sensors. A computer mouse can also basically be considered for controlling the x-ray arm 2. Furthermore pedals can also be used for control of the x-ray arm.

Since the feedback message is communicated to the user directly on activation of the joystick 10 and since the force effect 18 depends on the probability of the collision 13, the user can move the x-ray arm 2 almost without risk. It is further of advantage that the attention of the medical personnel and the peace and quiet of the patient are not adversely affected by distracting acoustic signals.

The concept described here can also be used in conjunction with x-ray devices which feature a number of x-ray arms 2. The moveable components for which collisions with an obstacle are to be avoided where possible can in addition also be components which record images in other wavelength ranges. Furthermore consideration can be given to controlling the magnets of a magnetic navigation device for controlling a magnetic tip of a catheter in the body of a patient in accordance with the concept described here.

The invention claimed is:

1. A device for medical provision of a patient, comprising:
   a medical unit movable relative to a patient bed;
   a position sensor that records the position of the medical unit;
   a supervision unit in communication with the position sensor that monitors the movement of the medical unit and generates a warning signal if a distance between the medical unit and an obstacle is near collision; and
   a guidance device that controls the movement of the medical unit via a user input, comprising a user operated guidance element that exerts a vibratory warning force perceivable in a tactile manner by the user based on the warning signal from the supervision unit, wherein the vibration amplitude increases as the distance between the medical unit and the obstacle decreases.

2. The device in accordance with claim 1, wherein the user operated guidance element comprises an inhibiting device that exerts an inhibiting force which acts against the force exerted by the user on the guidance element.

3. The device in accordance with claim 2, wherein the inhibiting force exerted by the inhibiting device increases as the distance of the medical unit to the obstacle decreases.

4. The device in accordance with claim 3, wherein the guidance device applies a control signal generated by the guidance element to the monitoring device.

5. The device in accordance with claim 4, wherein the medical unit is a movable x-ray arm having an x-ray source and an x-ray detector arranged at opposite ends of the arm.

6. The device in accordance with claim 5, wherein the medical unit is a magnetic navigation system with a magnet mounted on a support arm.

7. The device in accordance with claim 1, wherein guidance element is a joystick or a track ball.

8. A medical examination device, comprising:
   an patient examination table that supports a medical patient;

a medical unit that is movable relative to the examination table and provides or assists in providing a medical procedure;

a position sensor that records the position of the medical unit;

a supervision unit in communication with the position sensor that monitors the movement of the medical unit and generates a warning signal if the distance between the medical unit and an obstacle is near collision; and a guidance device that controls the movement of the medical unit via a user input, comprising a user operated guidance element that exerts a vibratory warning force perceivable in a tactile manner by the user based on the warning signal from the supervision unit, and applies a control signal generated by the guidance element to the monitoring device, wherein the vibration amplitude increases as the likelihood of a collision with an obstacle increases.

9. The device in accordance with claim 8, wherein the functional unit is a movable x-ray arm having an x-ray source and an x-ray detector arranged at opposite ends of the arm.

10. The device in accordance with claim 9, wherein the medical functional unit is a magnetic navigation system with a magnet mounted on a support arm.

11. The device in accordance with claim 8, wherein the guidance element is a joystick or a track ball.

* * * * *